US009463027B2

(12) United States Patent
Henderson (10) Patent No.: US 9,463,027 B2
(45) Date of Patent: Oct. 11, 2016

(54) AMPHIBIOUS TOURNIQUET DEVICES AND METHODS OF USE

(71) Applicant: Carson Thomas Henderson, Franklin, TN (US)

(72) Inventor: Carson Thomas Henderson, Franklin, TN (US)

( * ) Notice: Subject to any disclaimer, the term of this patent is extended or adjusted under 35 U.S.C. 154(b) by 0 days.

(21) Appl. No.: 14/869,992

(22) Filed: Sep. 29, 2015

(65) Prior Publication Data

US 2016/0089152 A1    Mar. 31, 2016

Related U.S. Application Data

(63) Continuation-in-part of application No. 14/726,579, filed on May 31, 2015, which is a continuation-in-part of application No. PCT/US2014/068675, filed on Dec. 5, 2014.

(60) Provisional application No. 61/912,460, filed on Dec. 5, 2013.

(51) Int. Cl.
*A61B 17/00* (2006.01)
*A61B 17/132* (2006.01)
*B63B 35/79* (2006.01)
*A61B 17/135* (2006.01)

(52) U.S. Cl.
CPC ......... *A61B 17/1327* (2013.01); *A61B 17/135* (2013.01); *A61B 17/1322* (2013.01); *A61B 17/1325* (2013.01); *B63B 35/7933* (2013.01); *B63B 2035/794* (2013.01)

(58) Field of Classification Search
CPC ....................... A61B 17/1327; A61B 17/1322
USPC ................................................. 606/201–204
See application file for complete search history.

(56) References Cited

U.S. PATENT DOCUMENTS

| 35,038 A * | 4/1862 | Pierce | A61B 17/1327 24/68 R |
| 1,447,967 A * | 3/1923 | Rutledge | A44B 11/25 24/163 R |
| 1,688,880 A * | 10/1928 | Pope | 2/50 |
| 1,870,052 A * | 8/1932 | Jones | A61B 17/1327 606/203 |
| 1,962,285 A | 6/1934 | Robinson | |

(Continued)

FOREIGN PATENT DOCUMENTS

| WO | 2015085124 A2 | 12/2014 |
| WO | 2015119968 A1 | 8/2015 |
| WO | 2016089446 | 6/2016 |

OTHER PUBLICATIONS

Written Opinion of the International Search Authority/US, issued May 22, 2015 on International Patent Application PCT/US14/68675, filed Dec. 5, 2014 in the name of Carson Thomas Henderson.

(Continued)

*Primary Examiner* — Amy R Weisberg
(74) *Attorney, Agent, or Firm* — Franklin & Associates International Inc; Matthew F. Lambrinos (57) ABSTRACT

Embodiments of the disclosure relate to tourniquet devices that have a strap which store an extension in a pocket. The extension can be deployed and wrapped around a ring of the strap to cinch the strap against an appendage to reduce blood flow below the tourniquet device. Some embodiments include a ratchet device that further constricts the appendage to reduce blood flow. These tourniquet devices can be worn in water and out of water and can be associated with various water sport accessories.

18 Claims, 8 Drawing Sheets

(56) References Cited

U.S. PATENT DOCUMENTS

| | | | | |
|---|---|---|---|---|
| 2,017,948 | A | * | 10/1935 | Chenery ............ A61B 17/1327 606/203 |
| 2,113,534 | A | * | 4/1938 | Brown ................ A61B 17/1327 606/203 |
| 2,339,239 | A | | 1/1944 | Carmichael |
| 2,363,138 | A | | 11/1944 | Moore |
| 2,756,753 | A | * | 7/1956 | Means ................ A61B 17/1327 128/885 |
| 2,812,123 | A | | 11/1957 | Girton |
| 4,041,562 | A | | 8/1977 | Nealy |
| 4,044,415 | A | | 8/1977 | Wood |
| 4,637,394 | A | * | 1/1987 | Racz .................... A61B 17/135 606/202 |
| 4,813,080 | A | * | 3/1989 | Toso .................. A41D 13/0007 2/44 |
| 4,938,040 | A | | 7/1990 | Humphreys, Jr. |
| 5,904,056 | A | | 5/1999 | Ozaki |
| 6,245,024 | B1 | * | 6/2001 | Montagnino ...... A61B 5/02233 600/499 |
| 6,471,560 | B2 | | 10/2002 | Kerckhoff |
| 6,899,720 | B1 | * | 5/2005 | McMillan .......... A61B 17/1322 606/203 |
| 6,960,223 | B1 | * | 11/2005 | Ambach ............ A61B 17/1327 606/203 |
| 7,947,061 | B1 | * | 5/2011 | Reis .................... A61B 17/1322 606/203 |
| 8,348,970 | B2 | | 1/2013 | Janota |
| 8,652,164 | B1 | * | 2/2014 | Aston ................ A61B 17/1327 606/203 |
| 9,168,044 | B2 | * | 10/2015 | Kirkham ............ A61B 17/1322 |
| 2003/0028215 | A1 | * | 2/2003 | Brooks .............. A61B 17/1327 606/203 |
| 2003/0139766 | A1 | * | 7/2003 | McEwen ............. A61B 17/135 606/203 |
| 2004/0173649 | A1 | | 9/2004 | Luedtke |
| 2005/0049630 | A1 | * | 3/2005 | Ambach ............ A61B 17/1327 606/203 |
| 2005/0113866 | A1 | * | 5/2005 | Heinz ................ A61B 17/1327 606/203 |
| 2005/0267518 | A1 | * | 12/2005 | Wright ................ A61B 17/132 606/203 |
| 2007/0005107 | A1 | | 1/2007 | Janota et al. |
| 2010/0049241 | A1 | * | 2/2010 | Persson ............. A61B 17/1327 606/203 |
| 2010/0057120 | A1 | | 3/2010 | Kirkham |
| 2010/0160957 | A1 | * | 6/2010 | Kirkham ............ A61B 17/1322 606/203 |
| 2011/0072545 | A1 | | 3/2011 | Bennett |
| 2011/0171861 | A1 | | 7/2011 | Roland |
| 2011/0270299 | A1 | * | 11/2011 | Rose ........................ A41D 1/08 606/203 |
| 2011/0271494 | A1 | | 11/2011 | Bellamy et al. |
| 2011/0295309 | A1 | | 12/2011 | Sullivan |
| 2011/0312233 | A1 | | 12/2011 | Starck, Jr. et al. |
| 2012/0215254 | A1 | | 8/2012 | Brub |
| 2012/0310273 | A1 | * | 12/2012 | Thorpe ............. A61B 17/1322 606/203 |
| 2013/0110019 | A1 | * | 5/2013 | Hopman ............. A61B 17/135 602/13 |
| 2015/0257767 | A1 | | 9/2015 | Henderson |

OTHER PUBLICATIONS

International Search Report of International Search Authority / US, issued May 22, 2015 on International Patent Application PCT/US14/68675, filed Dec. 5, 2014 in the name of Carson Thomas Henderson.

International Search Report and the Written Opinion of International Search Authority / US, issued Aug. 21, 2015 on International Patent Application PCT/US2015/033445, filed May 31, 2015 in the name of Carson Thomas Henderson.

Non-Final Office Action of Feb. 24, 2016, issued on US Patent Application No. 14/726579, filed May 31, 2015 in the name of Carson Thomas Henderson.

Swift-Strap LLC, Thor, webpage downloaded on Aug. 25, 2016 from the internet address http://www.thortq.com/, Swift-Strap llc, USA.

* cited by examiner

AMPHIBIOUS TOURNIQUET DEVICES AND METHODS OF USE

CROSS REFERENCE TO RELATED APPLICATIONS

This application is a continuation in part of U.S. Non-Provisional application Ser. No. 14/726,579, filed May 31, 2015, which is a continuation in part of International Patent Application PCT/US14/68675, filed Dec. 5, 2014, which claims the priority benefit of U.S. Provisional Application Ser. No. 61/912,460, filed on Dec. 5, 2013, all of which is hereby incorporated herein by reference including any reference cited therein.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERAL RIGHTS

N/A

TECHNICAL FIELD

Embodiments relate to accessories for medical emergencies in one or more applications such as but not limited to military applications and water sports, and to methods of operating said accessories. More particularly but not exclusively, embodiments relate to tourniquet devices.

SUMMARY

According to one aspect, a tourniquet device may comprise a strap that stores an extension section within a pocket, wherein the extension section may be movable from a stored position to a deployed position to increase or decrease a length of the strap. The extension section may be configured to loop around and secure to a surface of the strap such that the strap encircles an appendage of a user, the strap having a diameter when worn. A ratcheting device may be coupled to the strap that selectively decreases the diameter of the strap so as to exert compressive forces on the appendage and cut off blood flow of the appendage below the strap.

One general aspect includes a tourniquet device, including: (a) a strap including a primary section that stores an extension section, where the extension section is movable from a stored position to a deployed position to increase or decrease a length of the strap; (b) a ring disposed on an end of the strap, where the extension section is configured to loop around the ring and secure to a lower surface of the primary section such that the strap encircles an appendage of a user, the strap having a diameter when worn; and (c) a ratcheting device coupled to the strap that selectively decreases the diameter of the strap so as to exert compressive forces on the appendage and cut off or reduce blood flow of the appendage below the strap.

Other embodiments may include one or more of the following features. The tourniquet device where the ratcheting device includes a ratchet track and a ratchet buckle that traverses along the ratchet track. The tourniquet device where the ratchet buckle can be released to remove the compressive forces. The tourniquet device where the extension section is stored within a pocket of the primary section when the extension section is in the stored position. The tourniquet device further including an interface that receives a leash. The tourniquet device where the extension section includes complementary hook or loop fasteners that secure to hook or loop fasteners of an upper surface of the primary section when the extension section is in the deployed position.

The tourniquet device where at least a portion of a lower surface of primary section includes hook or loop fasteners that are configured to mate with hook or loop fasteners on an upper surface of the primary section to secure the strap around the appendage when the extension section is in the stored position. The tourniquet device where the extension section is provided with a pull tab.

The tourniquet device where the extension section includes a cover flap that mates with an upper surface of the primary section when the extension section is stored in the primary section. The tourniquet device where an internal end of the extension section is fixedly attached within the primary section. The tourniquet device further including a ring that joins the loop. The tourniquet device according further including a pull tab associated with a terminal end of the extension section.

The tourniquet device further including an interface that receives a leash. The tourniquet device according where the lower surface includes a section of elastomeric material and a section of hook or loop fasteners. The tourniquet device where the second section is overlapped by the lower surface to allow the section of hook or loop fasteners to engage with hook or loop fasteners of on the upper surface of the second section to dispose the strap in a circular configuration. The tourniquet device where the strap has a diameter that is selectively decreased by operation of the ratchet device.

One example embodiment includes a tourniquet device, including: (a) a strap that includes: a primary section that forms a lower surface of the strap, where a portion of the primary section overlaps itself to form a loop; and (b) a second section that is joined to an end of the portion of the primary section overlaps to form an upper surface, the second section being configured to releasably and securely mate with the lower surface, where the portion of the primary section overlaps is provided with a ratchet device that reduces a length of the strap; and (c) an extension section that is positioned between the primary section and the second section, the extension section capable of being placed into stored position or a deployed position.

Other embodiments may include one or more of the following features. The tourniquet device further including a ring that joins the loop. The tourniquet device further including a pull tab associated with a terminal end of the extension section. The tourniquet device further including an interface that receives a leash. The tourniquet device where the lower surface includes a section of elastomeric material and a section of hook or loop fasteners. The tourniquet device where the second section is overlapped by the lower surface to allow the section of hook or loop fasteners to engage with hook or loop fasteners of on the upper surface of the second section to dispose the strap in a circular configuration. The tourniquet device where the strap has a diameter that is selectively decreased by operation of the ratchet device.

In one more of more of the aforementioned embodiments of the tourniquet device the hook and loop fasteners may be omitted.

BRIEF DESCRIPTION OF THE DRAWINGS

Certain embodiments of the present disclosure are illustrated by the accompanying figures. It will be understood

DETAILED DESCRIPTION

Embodiments relate to accessories for medical emergencies in one or more applications such as but not limited to military applications and water sports, and to methods of operating said accessories. More particularly but not exclusively, embodiments relate to tourniquet devices.

Embodiments of the disclosure relate to tourniquet devices that have a strap which store an extension in a pocket. The extension can be deployed and wrapped around a ring of the strap to cinch the strap against an appendage to reduce blood flow below the tourniquet device. Some embodiments include a ratchet device that further constricts the appendage to reduce blood flow. These tourniquet devices can be worn in water and out of water and can be associated with various water sport accessories.

In one or more aspects, the tourniquet device has a strap that stores an extension section within a pocket, wherein the extension section is movable from a stored position to a deployed position to increase or decrease a length of the strap. The extension section is configured to loop around and secure to a surface of the strap such that the strap encircles an appendage of a user, the strap having a diameter when worn. A ratcheting device is coupled to the strap that selectively decreases the diameter of the strap so as to exert compressive forces on the appendage and cut off blood flow of the appendage below the strap.

Figure 1:
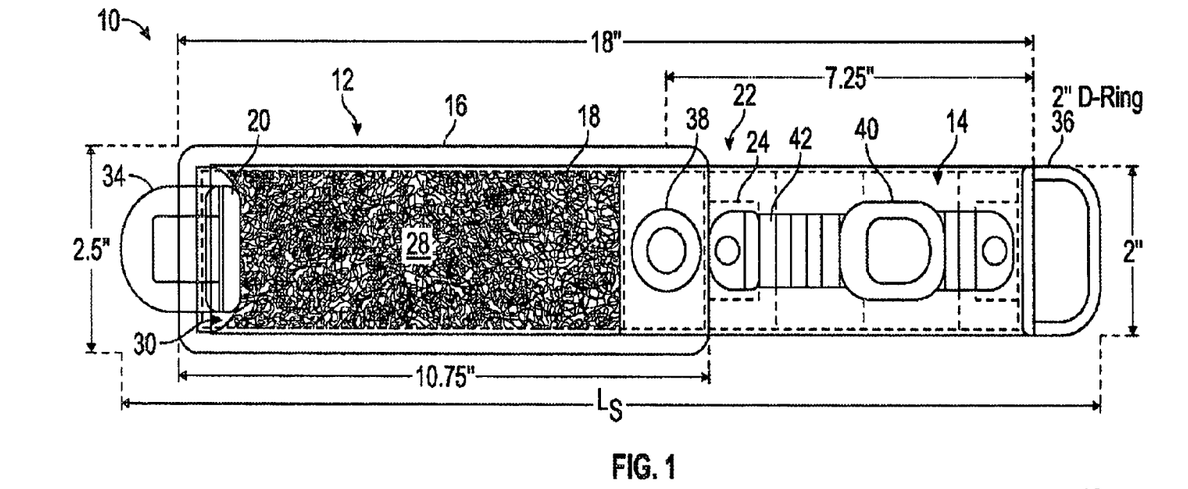
FIG. 1 is a front elevation view of an example tourniquet device in a stored configuration, constructed in accordance with the present disclosure.
Figure 2:
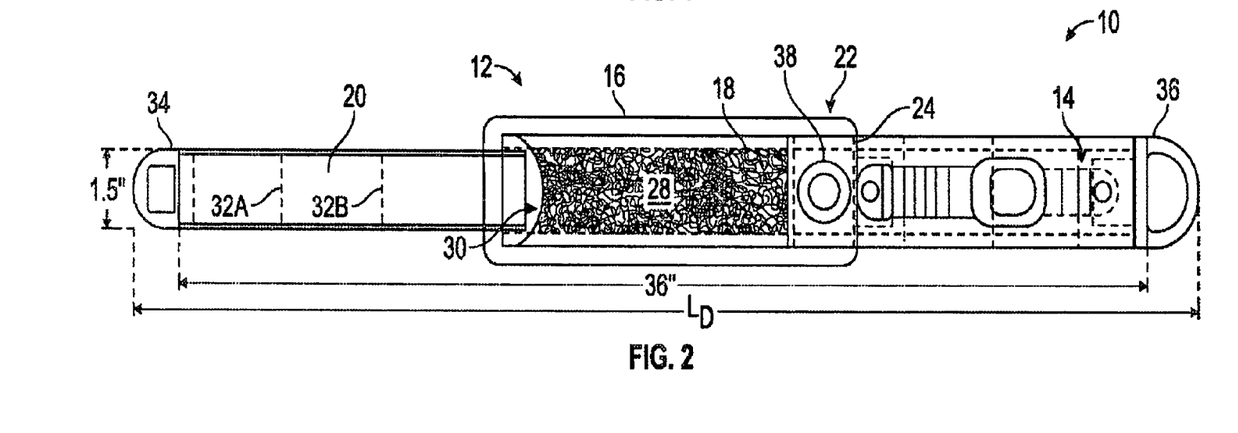
FIG. 2 is a front elevation view of the example tourniquet device of FIG. 1 in an extended configuration.

Referring now collectively to FIGS. 1 and 2 which illustrates an embodiment of a tourniquet device 10. The tourniquet device 10 comprises a strap 12 and ratchet device 14. The strap comprises a primary section 16, a second section 18, and an extension section 20, in some embodiments.

According to some embodiments, strap 12 has an upper surface 22 that is divided into segments. In one embodiment, the upper surface 22 is comprised of a portion 24 of the primary section 16 that overlaps the remainder of the primary section 16. The remainder of the primary section 16 forms a rear surface 26 of the strap 12 (see FIGS. 3-4).

In some embodiments, the ratchet device 14 is joined to the portion 24 of the primary section 16. Hook or loop fasteners (e.g., VELCRO) 28 are disposed on an upper surface of the second section 18.

According to some embodiments, the second section 18 and primary section 16 are joined together at their upper and lower edges to create a pocket 30. The extension section 20 is stored within the pocket 30 when the extension section 20 is in a stored configuration. When the extension section 20 is in a deployed configuration the extension section 20 is extended from storage within the pocket 30. In one embodiment, the extension section 20 can be folded in an overlapping manner along fold lines 32A and 32B for storage. In another embodiment, the extension section 20 is elastomeric and retracts within the pocket 30 when no pulling force is being exerted on the extension section 20.

In some embodiments, the extension section 20 comprises a pull tab 34 that allows a user to extract the extension section from the pocket 30. Deployment of the extension section 20 functions to increase an overall length LD of the strap 12 compared with its overall length when the Ls when the extension section 20 is in its stored configuration.

According to some embodiments, the primary section 16 is provided with a ring 36 that extends from an end that is opposite of the pull tab 34 of the extension section 20.

Figure 9:
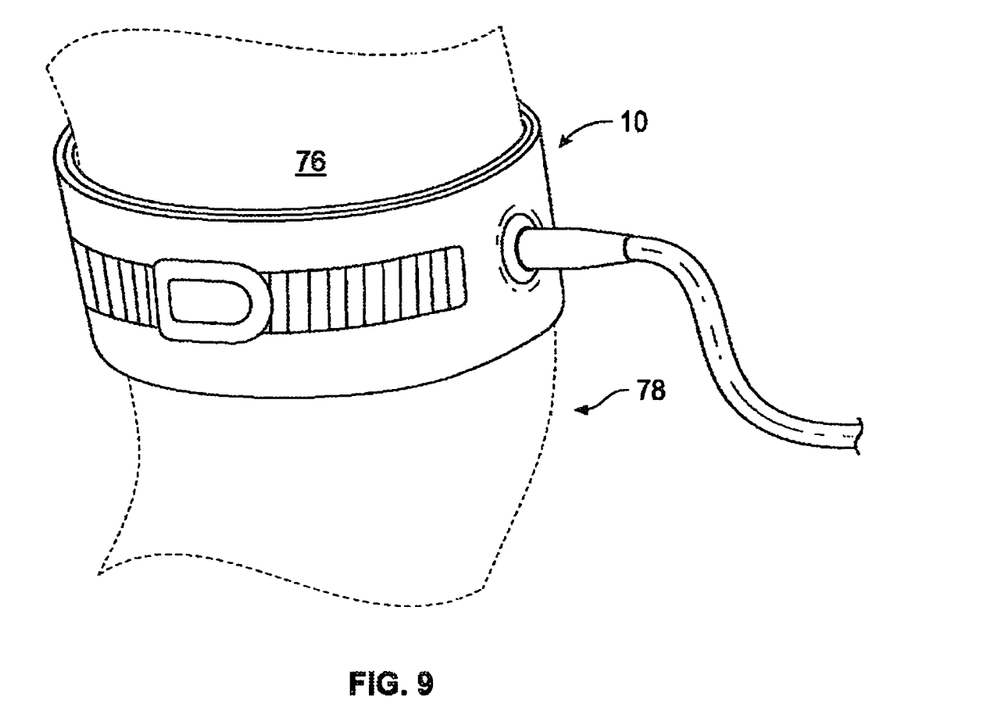
FIG. 9 is a perspective view of the tourniquet device of FIGS. 1-8 in a worn configuration around an ankle of a user.

In some embodiments, the tourniquet device 10 comprises an interface 38 that allows the strap 12 to couple with a leash, such as a surf leash as illustrated in FIG. 9. In this embodiment, the tourniquet device 10 functions as a water sport device. The tourniquet device 10 can couple with any appropriately configured water sport accessory such as a surf board, boogie board, knee board, wake board, wake skate, or other similar water sport accessory.

In accordance with the present disclosure, the ratchet device 14 can comprise a ratchet buckle 40 that can traverse along a ratchet track 42. In one embodiment, the ratchet track is a ladder strap. The ratchet device 12 is fixedly coupled to the portion 24 of the primary section 16 of the strap 12. Thus, actuation of the ratchet buckle 40 will reduce a length of the strap as the ratchet buckle 40 traverses along a ratchet track 42. When the strap 12 is worn by a user around an appendage the ratchet device 14 functions to reduce a diameter of the strap 12 by shortening a length of the strap 12. This reduction in diameter exerts compressive forces to reduce or cut off blood flow to the appendage below the tourniquet device 10. Thus, when the user suffers an injury that leads to excessive blood loss, the tourniquet device 10 can be placed above the injury and tightened as needed to reduce or cut off blood flow to the injury.

The ratchet buckle 40 can also be actuated by the user to loosen the strap 12, if needed. Additional use cases are provided in greater detail infra with respect to the description of FIGS. 8 and 9.

Figure 3:
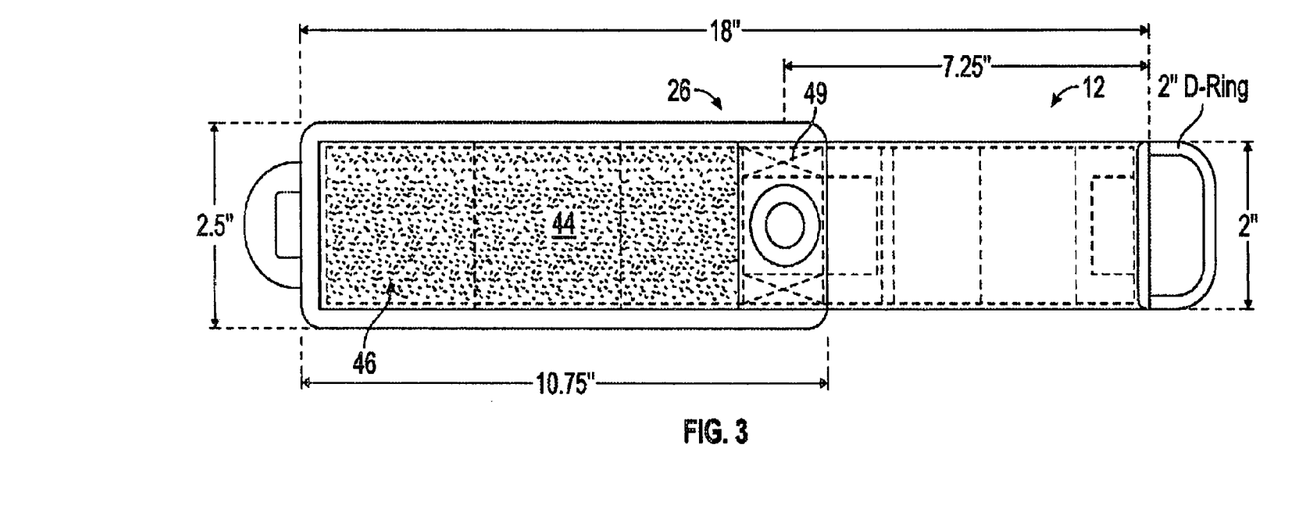
FIG. 3 is a rear elevation view of the example tourniquet device of FIGS. 1-2 in a stored configuration.
Figure 4:
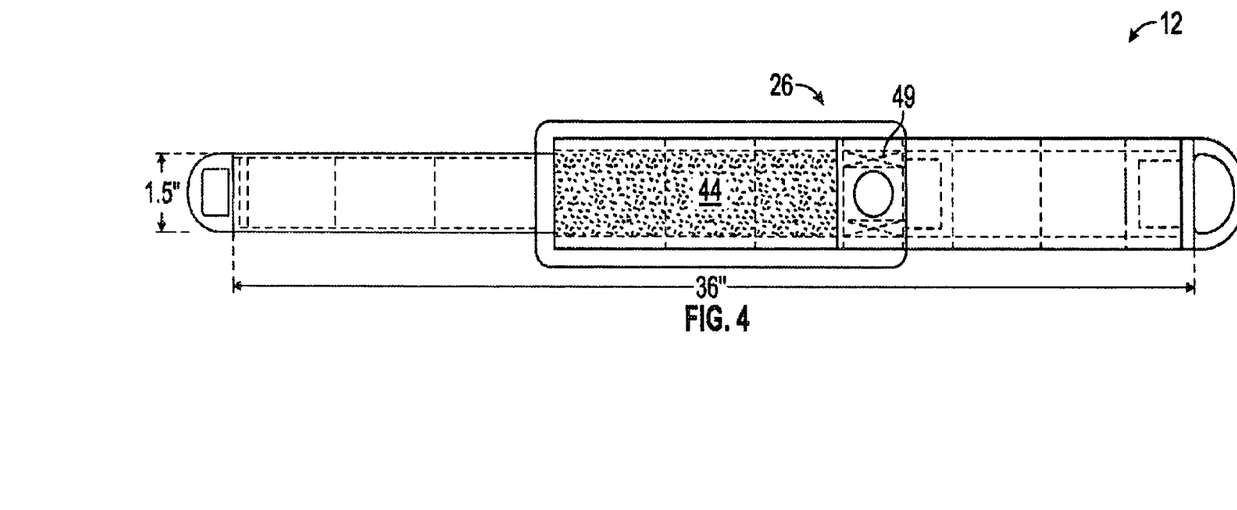
FIG. 4 is a rear elevation view of the example tourniquet device of FIG. 1-3 in an extended configuration.

Referring now to FIGS. 3 and 4, the rear surface 26 of the strap 12 is illustrated. In some embodiments, a portion 44 of the primary section 16 is provided with hook or loop fasteners 46. The hook or loop fasteners 46 of the portion 44 are configured to mate with the hook or loop fasteners 28 disposed on the upper surface of the second section 18. FIGS. 3 and 4 also illustrate an embodiment of a stitching pattern 49 that joins the various components of the tourniquet device together.

Figure 5:
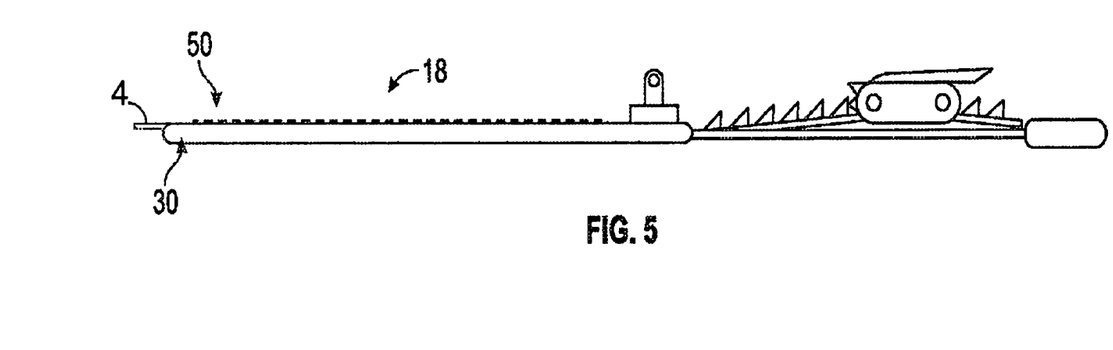
FIG. 5 is a side elevation view of the example tourniquet device of FIGS. 1-4 in a stored configuration.
Figure 6:
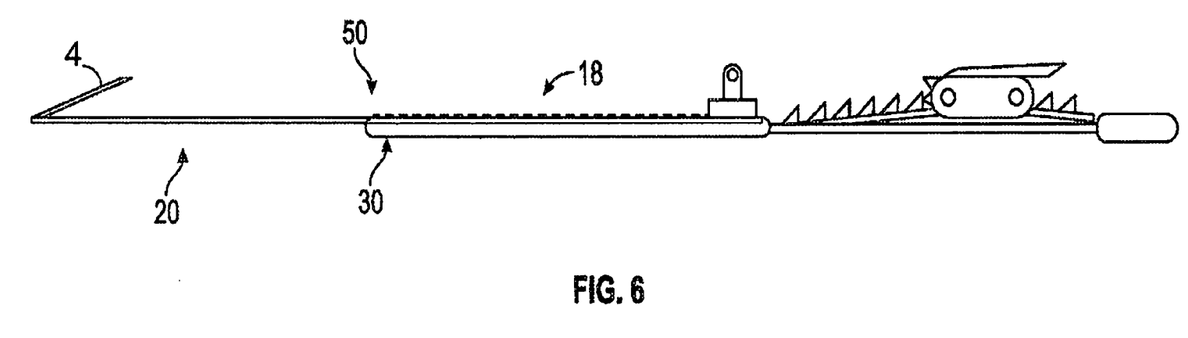
FIG. 6 is a rear elevation view of the example tourniquet device of FIG. 1-5 in an extended configuration.

As best illustrated in FIGS. 5 and 6, in some embodiments, the extension section 20 comprises a cover flap 4 that mates with an upper surface 50 of the second section 18 when the extension section 20 is stored in the pocket 30.

Figure 7:
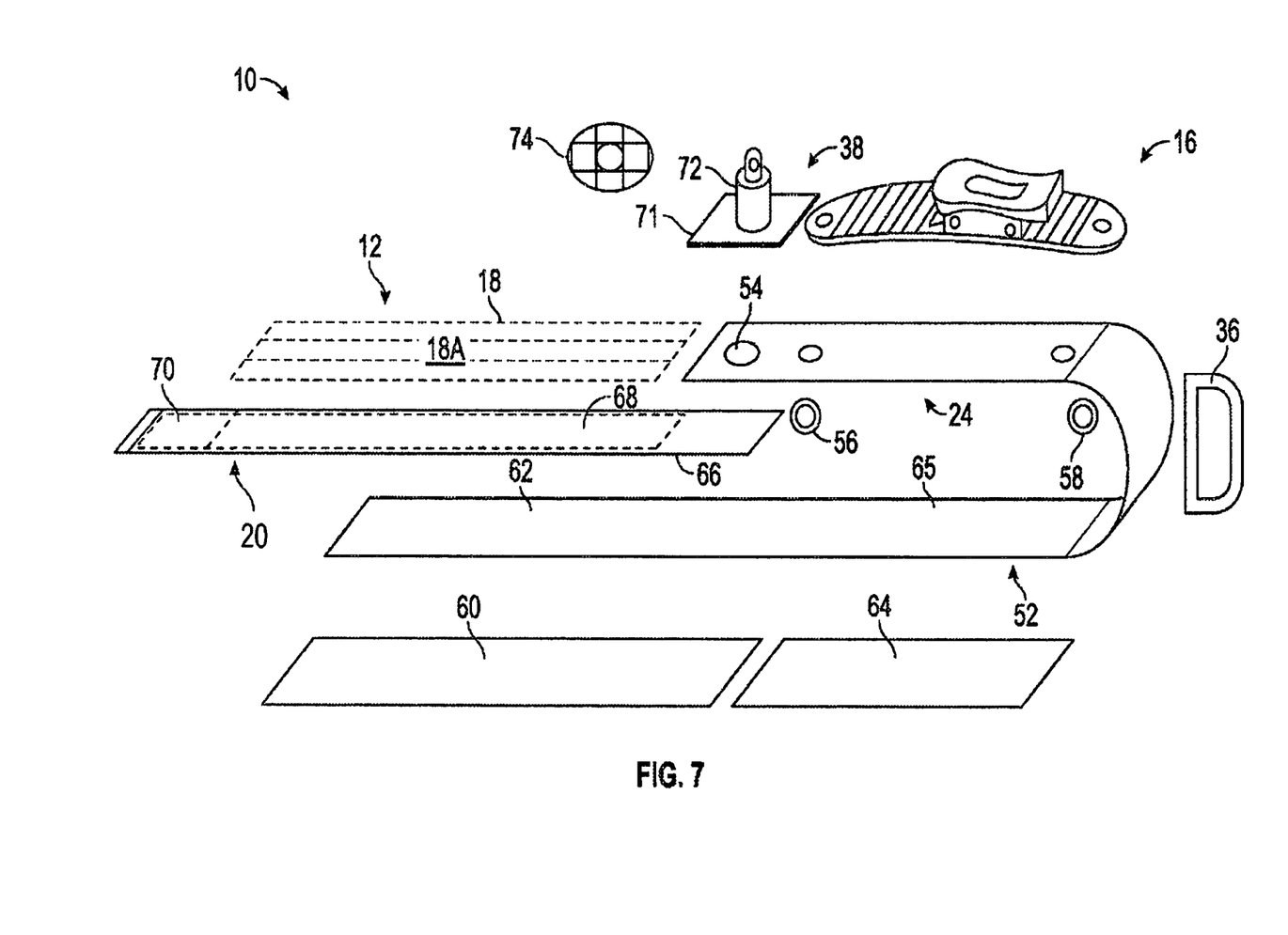
FIG. 7 is an exploded view of the example tourniquet device of FIGS. 1-6.

FIG. 7 illustrates an exploded and detailed view of the tourniquet device 10. The primary section 16 includes has a lower portion 52 and the portion 24 that at least partially overlaps the lower portion 52. The primary section 16 can be constructed from a nylon webbing material or other suitable durable material. A terminal end of the portion 24 includes an aperture 54 that receives the interface 38 therethrough.

The ratchet device 14 can be joined to the portion 24 with rivets 56 and 58 or other suitable fastening means.

In some embodiments, the primary section 16 is threaded into the ring 36 such that the ring 36 is disposed where the lower portion 52 and portion 24 overlap one another.

A layer 60 of neoprene and LYCRA material can be attached to one section 62 of the lower portion 52, while a layer 64 of loop VELCRO is applied to a second section 65 of the lower portion 52.

The second section 18 of the strap 12 is joined to the portion 24 of the primary strap 16. The second section 18 has an upper surface 18A that is provided with a covering of hook or loop VELCRO fasteners.

The extension section 20 comprises a substrate 66 created from a nylon webbing material (or other suitable material). A section 68 of loop VELCRO can be attached to the substrate 66 and a section 70 of hook VELCRO can be attached to substrate 66 near its terminal end.

In some embodiments, the interface 38 comprises a base plate 71 and connector 72. The base plate 71 is sandwiched between the substrate 66 and portion 24 of the primary section 16. In some embodiments, a grommet 74 is installed on the connector 72 for support. The grommet 74 can be manufactured from rubber or another suitable elastomeric material.

In some embodiments, the layer 60 is attached to the lower portion 52 of the primary section 16 of the strap 12. The layer 60 can extend in its width somewhat wider than the lower portion 52 so that a LYCRA edging can be attached. Also in addition to edge stitching there can be cross width stitching to create compartments so that if there is a stitching failure there is not a complete failure.

Next, the layer 64 is attached to the lower portion 52 and edge and cross width stitching are completed. The ring 36 is then slid over the primary section 16, and positioned at the overlapping end. The ratchet track is then riveted and stitched to the primary section 16.

The sections of the extension section 20 are then assembled.

A pocket is created by stitching the second section 18 to the primary section 16 of the strap 12. The interface 38 (specifically the base plate) is inserted inside of the pocket and the connector cylinder 70 is placed through the aperture 54. A non-VELCRO end of the substrate 66 is placed underneath the base plate of the interface 38. Stitching is sewn width ways across base plate to secure the same. Stitching is placed for the remaining length of the primary section with the second section 18 to form one continuous strap, with the extension section and interface secured within.

The rubber grommet 74 can be sewn over the connector 72. Additional stitching is provided as needed for securement of various components of the tourniquet device 10.

Figure 8:
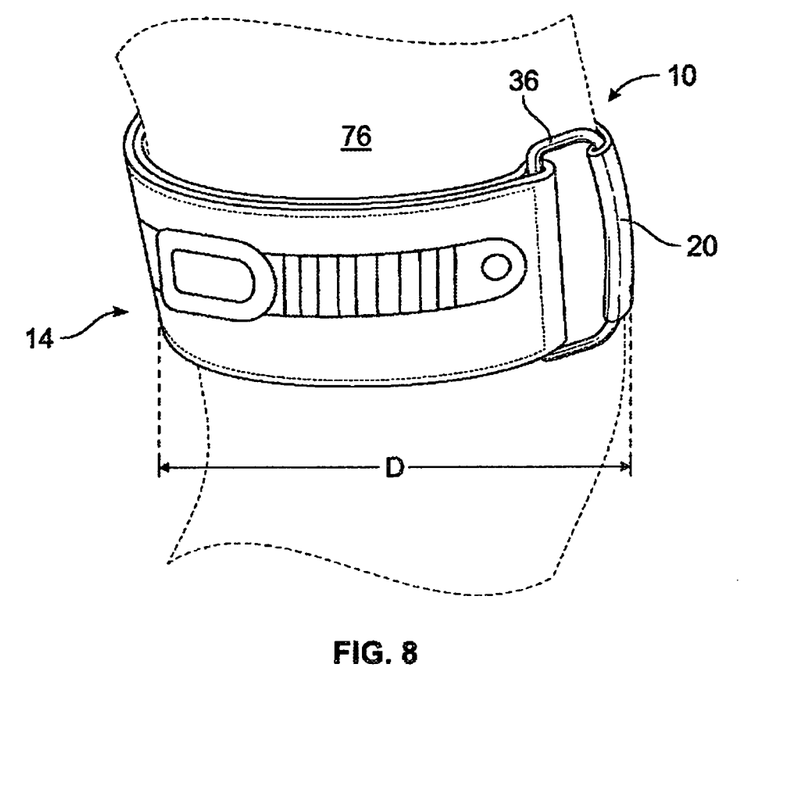
FIG. 8 is a perspective view of the tourniquet device of FIGS. 1-7 in a worn configuration with the ratchet device constricting an appendage.

FIG. 8 illustrates the tourniquet device 10 in association with an appendage 76, functioning as a tourniquet. In this embodiment, the extension section 20 has been extended to the deployed position (see FIGS. 2, 4, and 6). The extension section 20 has been looped into the ring 36 and overlapped back onto an upper surface 18A of the second section 18 (see FIG. 7). The user can utilize the ratchet device 14 to compress the appendage 76 and reduce/cut off blood flow below the tourniquet device 10. This compression is caused by the ratchet device 14 decreasing an overall length of the strap 12, which effectively causes a diameter D of the strap to decrease.

FIG. 9 illustrates the tourniquet device 10 in association with an appendage 76, functioning as a surf leash. The tourniquet device 10 encircles an ankle 78. In this configuration, the extension section 20 (not show in this embodiment) is in the stored configuration. The lower portion 52 (see FIGS. 1-7) that is provided with hook or loop VELCRO fasteners can be overlapped onto the second section 18 which also comprises complementary hook or loop VELCRO fasteners.

Figure 10:
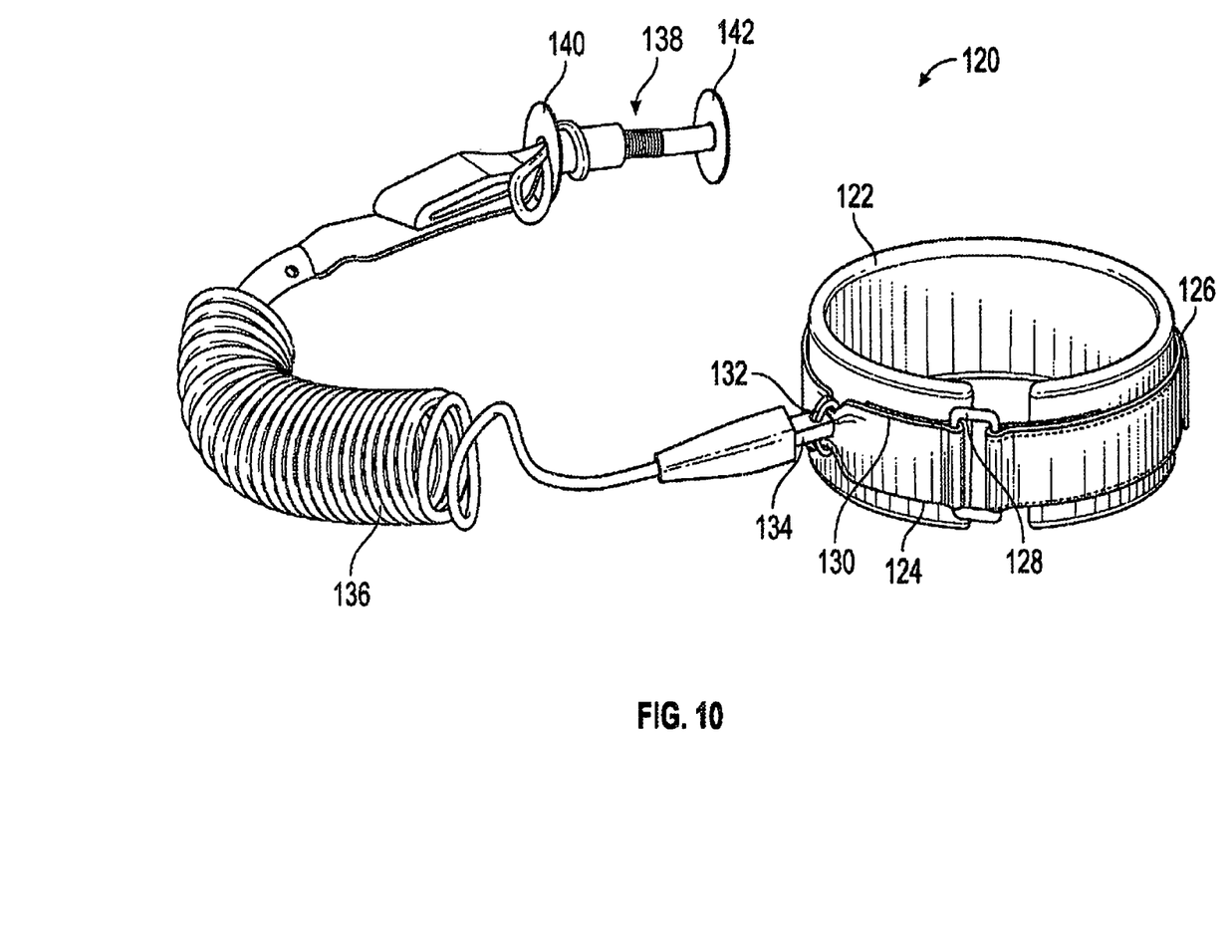
FIG. 10 is a perspective view of another embodiment of a tourniquet device, constructed in accordance with the present disclosure.

FIG. 10 illustrates another embodiment of a tourniquet device 120. The tourniquet device 120 comprises a primary section 122, a secondary section 124, and an extension section 126. The tourniquet device 120 also comprises a buckle 128 that receives the extension section 126 in such a way that extension section 126 can be looped back around and tightened around a user's appendage. The primary section 122 is provided with a ring strap 130 that is attached on its opposing ends to the primary section 122. In contrast with the embodiments of FIGS. 1-9, the tourniquet device 120 comprises a connector ring 132 that mates with the ring strap 130. The connector ring 132 further comprises a quick connector 134 that allows for quick association/dissociation with a leash 136. The leash 136 can mate with a water sport accessory such as a surfboard using an accessory connector 138. The accessory connector 138 can comprise a female pedestal 140 that joins with the leash 136 and a male threaded pedestal 142 that threadably mates with the female pedestal 140. The male threaded pedestal 142 can be fixedly associated with a water sport accessory such as a surfboard. The tourniquet device 120 is coupled with the water sport accessory by threadably mating the male and female pedestals of the accessory connector 138 with one another.

Figure 11:
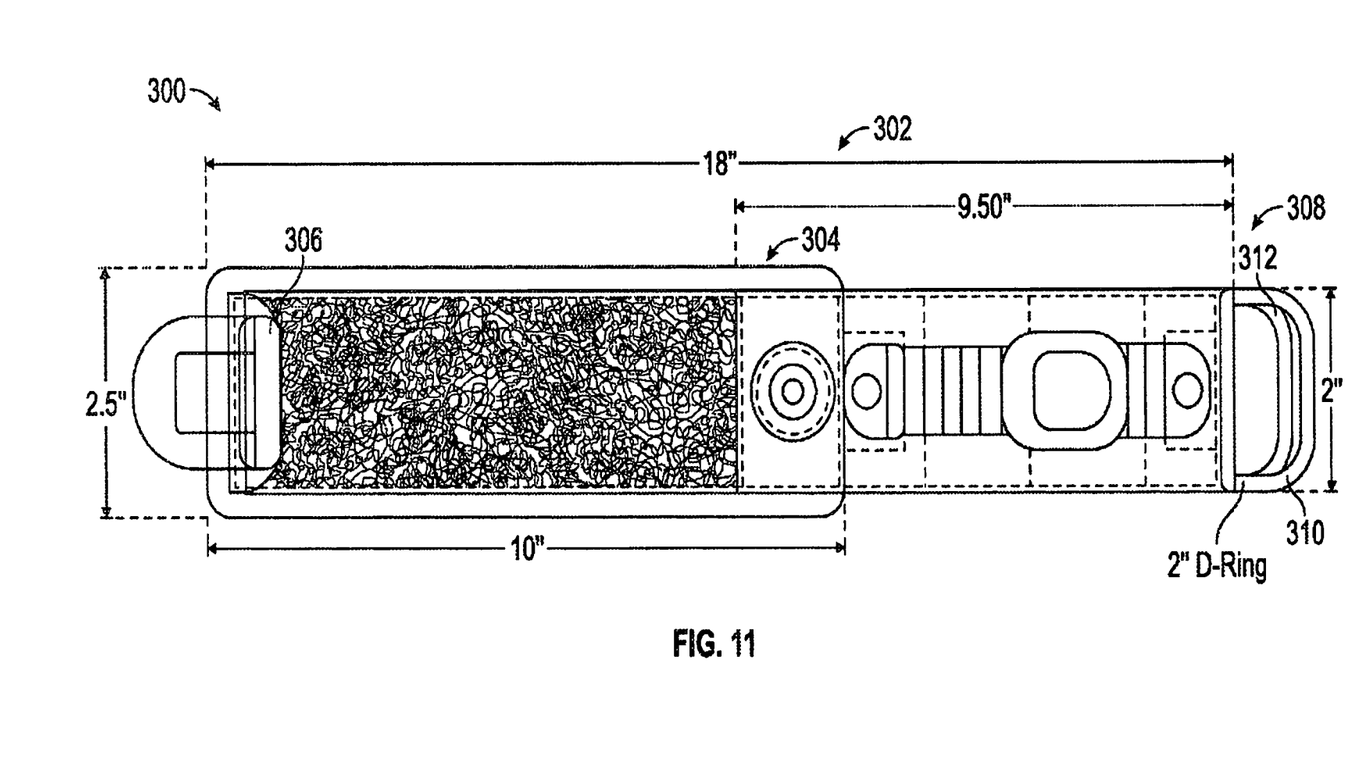
FIG. 11 is a top plan view of another embodiment of a tourniquet device, constructed in accordance with the present disclosure.

FIG. 11 illustrates another embodiment of a tourniquet device 300. The tourniquet device 300 comprises a primary section 302, a secondary section 304, and an extension section 306. The tourniquet device 300 also comprises a double ring buckle 308 that receives the extension section 306 in such a way that extension section 306 can be lockingly looped around the double ring buckle 308. In some embodiments, the primary section 302, a secondary section 304, and an extension section 306 need not include hook or loop fasteners for securement of the extension section 306 when the tourniquet device 300 is engaged to compress an appendage. The extension section 306 can be threaded behind both exposed surfaces of the two buckles, wrapped around a top buckle 310 and through the bottom buckle 312 to lock the tourniquet device 300 into its compressed configuration.

In some embodiments, the secondary section 304 can include hook and loop fasteners that mate with hook and loop fasteners of the extension section 306 to provide a secondary or failsafe securement mechanism. Thus, after the extension section 306 is lockingly looped through the double ring buckle 308, the extension section 306 can be secured to the secondary section 304 for securement via hook and loop fastening. In some embodiments, the tourniquet device 300 is the same as the tourniquet device of embodiment of FIG.

1 except for ring or buckle 36 replaced with a double buckle configuration as shown in FIG. 11.

In yet other embodiments, the tourniquet devices of the accompanying figures do not include hook and loop fasteners.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A tourniquet device, comprising:
    a strap that stores an extension section within a pocket, wherein the extension section is movable from a stored position to a deployed position to increase or decrease a length of the strap, wherein the extension section is fixedly attached within the pocket by a first end and extendable from the pocket using a second end to extend a length of the strap;
    a ring disposed on an end of the strap, wherein the extension section is configured to loop around the ring and secure to a lower surface of a primary section of the strap such that the strap encircles an appendage of a user, the strap having a diameter when worn;
    a ratcheting device coupled to the strap that selectively decreases the diameter of the strap so as to exert compressive forces on the appendage and cut off blood flow of the appendage below the strap;
    a surf leash; and
    an interface for the surf leash extending from an outer surface of the strap, the interface comprising:
        a base plate integrated into the strap; and
        a tubular connector extending perpendicularly from the base plate, the tubular connector being configured to mate with the surf leash.

2. The tourniquet device according to claim 1, wherein the ratcheting device includes a ratchet track and a ratchet buckle that traverses along the ratchet track.

3. The tourniquet device according to claim 2, wherein the ratchet buckle can be released to remove the compressive forces.

4. The tourniquet device according to claim 1, wherein the extension section is stored within the pocket formed by a second section that is joined to a portion of the primary section.

5. The tourniquet device according to claim 1, further comprising an interface that receives a leash.

6. The tourniquet device according to claim 1, wherein the extension section comprises complementary hook or loop fasteners that secure to hook or loop fasteners of an upper surface of the primary section when the extension section is in the deployed position.

7. The tourniquet device according to claim 1, wherein the extension section is provided with a pull tab.

8. The tourniquet device according to claim 1, wherein at least a portion of a lower surface of primary section comprises hook or loop fasteners that are configured to mate with hook or loop fasteners on an upper surface of a second section to secure the strap around the appendage when the extension section is in the stored position, wherein the second section is joined to the primary section.

9. The tourniquet device according to claim 1, wherein the extension section comprises a cover flap that mates with an upper surface of the second section when the extension section is stored in the pocket.

10. The tourniquet device according to claim 1, wherein an internal end of the extension section is fixedly attached within the pocket.

11. A tourniquet device, comprising:
    a strap that comprises:
        a primary section that forms a lower surface of the strap, wherein a portion of the primary section overlaps itself to form a loop; and
        a second section that is joined to an end of the portion of the primary section that overlaps to form an upper surface, the second section being configured to releasably and securely mate with the lower surface of the primary section, wherein the portion of the primary section that overlaps is provided with a ratchet device that reduces a length of the strap; and
        an extension section that is positioned between the primary section and the second section, and within a pocket of the strap, the extension section capable of being placed into a stored position or a deployed position, wherein the extension section is fixedly attached within the pocket by a first end and extendable from the pocket using a second end to extend a length of the strap;
    a surf leash; and
    an interface for the surf leash extending from an outer surface of the strap, the interface comprising:
        a base plate integrated into the strap; and
        a tubular connector extending perpendicularly from the base plate, the tubular connector being configured to mate with the surf leash.

12. The tourniquet device according to claim 11, further comprising a ring that joins the loop.

13. The tourniquet device according to claim 11, further comprising a pull tab associated with a terminal end of the extension section.

14. The tourniquet device according to claim 11, further comprising an interface that receives a leash.

15. The tourniquet device according to claim 11, wherein the lower surface comprises a section of elastomeric material and a section of hook or loop fasteners.

16. The tourniquet device according to claim 15, wherein the second section is overlapped by the lower surface to allow the section of hook or loop fasteners to engage with hook or loop fasteners of on the upper surface of the second section to dispose the strap in a circular configuration.

17. The tourniquet device according to claim 15, wherein the strap has a diameter that is selectively decreased by operation of the ratchet device.

18. A tourniquet device, comprising:
- a strap that stores an extension section within a pocket, wherein the extension section is movable from a stored position to a deployed position to increase or decrease a length of the strap, wherein the extension section is fixedly attached within the pocket by a first end and extendable from the pocket using a second end to increase the length of the strap;
- wherein the extension section is configured to loop around and secure to a surface of the strap such that the strap encircles an appendage of a user, the strap having a diameter when worn; and
- a ratcheting device coupled to the strap that selectively decreases the diameter of the strap so as to exert compressive forces on the appendage and cut off blood flow of the appendage below the strap;
- a surf leash; and
- an interface for the surf leash extending from an outer surface of the strap, the interface comprising:
  - a base plate integrated into the strap; and
  - a tubular connector extending perpendicularly from the base plate, the tubular connector being configured to mate with the surf leash.

\* \* \* \* \*